(12) United States Patent
Vogelstein et al.

(10) Patent No.: US 7,354,703 B2
(45) Date of Patent: Apr. 8, 2008

(54) SECURIN IS REQUIRED FOR CHROMOSOMAL STABILITY IN HUMAN CELLS

(75) Inventors: Bert Vogelstein, Baltimore, MD (US); Kenneth W. Kinzler, Bel Air, MD (US); Prasad Jallepalli, Baltimore, MD (US); Christoph Lengauer, Columbia, MD (US)

(73) Assignee: The Johns Hopkins University, Baltimore, MD (US)

( * ) Notice: Subject to any disclaimer, the term of this patent is extended or adjusted under 35 U.S.C. 154(b) by 1218 days.

(21) Appl. No.: 09/815,340

(22) Filed: Mar. 23, 2001

(65) Prior Publication Data

US 2002/0137018 A1    Sep. 26, 2002

(51) Int. Cl.
| G01N 33/78 | (2006.01) |
|---|---|
| C12Q 1/00 | (2006.01) |
| C12N 5/00 | (2006.01) |
| C12N 5/02 | (2006.01) |
| C01N 33/78 | (2006.01) |
| C12Q 1/00 | (2006.01) |
| C12N 5/00 | (2006.01) |
| C12N 5/02 | (2006.01) |

(52) U.S. Cl. ............... 435/4; 435/375; 436/63; 436/64

(58) Field of Classification Search ............ 435/4, 435/366; 530/358
See application file for complete search history.

(56) References Cited

FOREIGN PATENT DOCUMENTS

WO    WO98/22587    *    5/1998

OTHER PUBLICATIONS

Morales et al, Oncogene, Jan. 20, 2000, vol. 19, pp. 403-409.*
Zur et al, EMBO, Feb. 15, 2000, vol. 20, pp. 792-801.*
Lengauer et al, Nature, 1998, vol. 396, pp. 643-649.*
Andrew Bush et al, "c-myc null cells misregulate cad and gadd45 but not other proposed c-Myc targets", Genes & Development, vol. 12, 1998, pp. 3797-3802.

Hitoshi Matsushime et al, "Identification and Properties of an Atypical Catalytic Subunit ($p34^{PSK-J3}$/cdk4) for Mammalian D Type G1 Cyclins", Cell, vol. 71, 1992, pp. 323-334.
Martins Eilers et al, "The MYC protein activates transcription of the $\alpha$-prothymosin gene", The EMBO Journal, vol. 10, No. 1, 1991, pp. 133-141.
Mark E. Ewen et al, "TGF$\beta$ Inhibition of Cdk4 Synthesis Is Linked to Cell Cycle Arrest", Cell, vol. 74, 1993, pp. 1009-1020.
Heiko Hermeking et al, "Abrogation of p53-induced cell cycle arrest by c-Myc: evidence for an inhibitor of p21", Oncogene, vol. 11, 1995, pp. 1409-1415.
Kathryn M. Latham et al, "Inhibition of p53-Mediated Growth Arrest by Overexpression of Cyclin-Dependent Kinases", Molecular and Cellular Biology, vol. 16, No. 8, 1996, pp. 4445-4455.
Jim Wang et al, "Myc activates telomerase", Genes & Development, vol. 12, 1998, pp. 1769-1774.
Abdel G. Elkahloun et al, "Transcrpit Mapping in a 46-kb Sequenced Region at the Core of 12q13.3 Amplification in Human Cancers", Genomics, vol. 42, 1997, pp. 295-301.
Maria K. Mateyak et al, "Phenotypes of c-Myc-deficient Rat Fibroblasts Isolated by Targeted Homologous Recombination", Cell Growth & Differentiation, vol. 8, 1997, pp. 1039-1048.
Philipp Steiner et al, "Identification of a Myc-dependent step during the formation of active $G_1$ cyclin-cdk complexes", The EMBO Journal, vol. 14, No. 19, 1995, pp. 4814-4826.
Eric C. Holland et al, "Modeing mutations in the $G_1$ arrest pathway in human gliomas: oxerexpression of CDK4 but not loss of IND4aARF induces hyperploidy in cultured mouse astrocytes", Genes & Development, vol. 12, 1998, pp. 3644-3649.
Maria K. Mateyak et al, c-Myc Regulates Cyclin D-Cdk4 and -Cdk6 Activity but Affects Cell Cycle Progression at Multiple Independent Points, Molecular and Cellular Biology, vol. 19, No. 7, 1999, pp. 4672-4683.
Jaromir Vlach et al, "Growth arrest by the cyclin-dependent kinase inhibitor p27 KIP1 is abrogated by c-Myc", The EMBO Journal, vol. 15, No. 23, 1996, pp. 6595-6604.

* cited by examiner

*Primary Examiner*—Karen A. Canella
(74) *Attorney, Agent, or Firm*—Banner & Witcoff, Ltd.

(57) ABSTRACT

Securin-deficient cells and their isogenic securin-proficient counterparts are useful for screening potential anti-tumor agents. Potential therapeutic agents are screened for the ability to preferentially inhibit or kill a securin-deficient cell. The association of securin deficiency and chromosomal instability leading to aneuploidy, renders securin an excellent target for chemotherapeutic drug development.

10 Claims, 13 Drawing Sheets
(1 of 13 Drawing Sheet(s) Filed in Color)

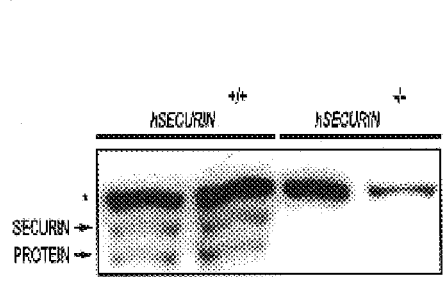
FIG. 1D
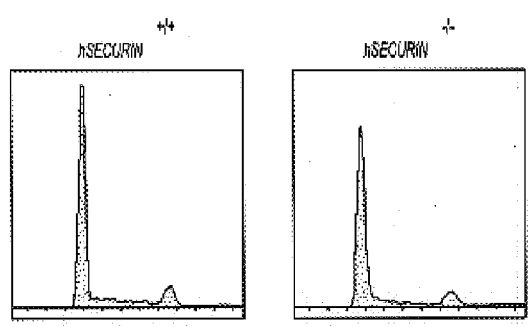
FIG. 1E
| hSECURIN | FACS ANALYSIS (%) | | | CYTOLOGY (%) | | |
|---|---|---|---|---|---|---|
| | G1 | S | G2/M | APOPTOSIS | MITOSIS | INTERPHASE |
| +/+ | 69 | 17 | 14 | 2 | 1 | 97 |
| -/- | 70 | 16 | 14 | 1.8 | 0.7 | 97.5 |
FIG. 1F

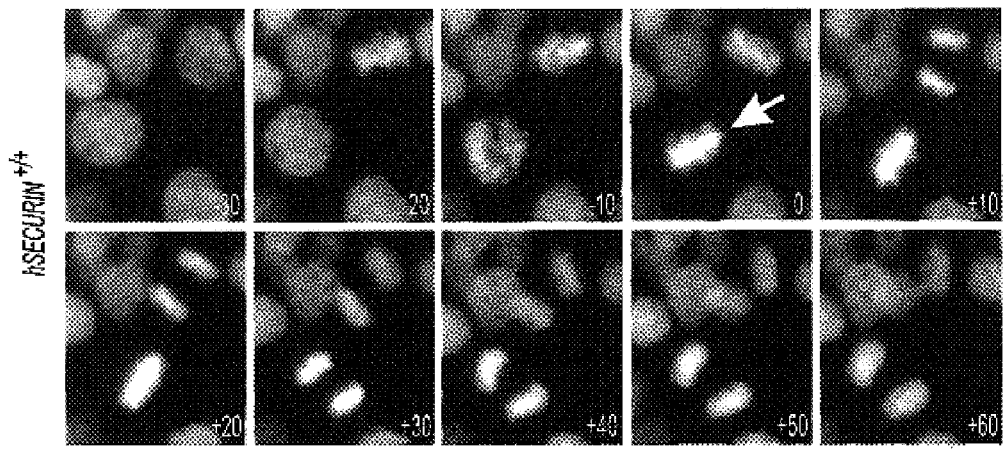
FIG. 4A
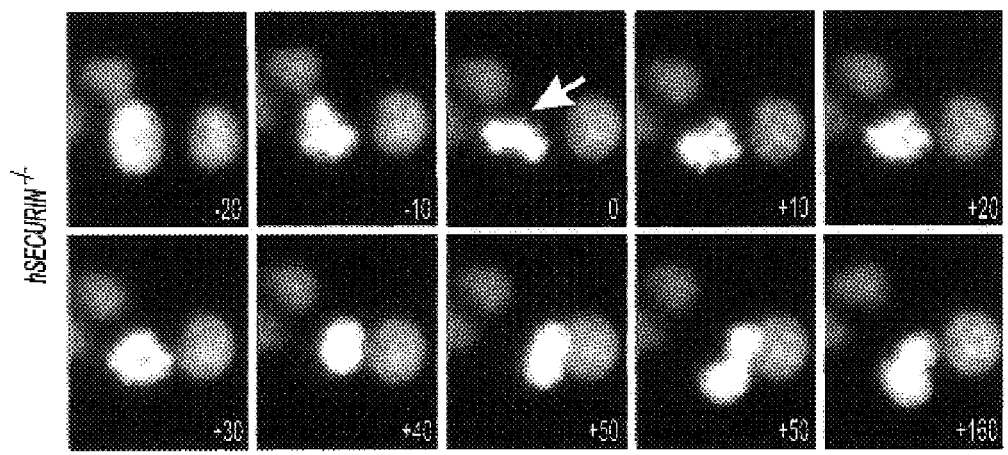
FIG. 4B
| MITOTIC INTERVAL (MINUTES) | hSECURIN +/+ | hSECURIN -/- |
|---|---|---|
| PROPHASE TO METAPHASE | 15 | 19 |
| METAPHASE TO ANAPHASE | 21 | 57 |
| ANAPHASE TO TELOPHASE | 17 | 16 |
FIG. 4C

SECURIN IS REQUIRED FOR CHROMOSOMAL STABILITY IN HUMAN CELLS

The U.S. Government has certain rights in this invention as provided for by the terms of Grant No. CA 43460 awarded by the National Institutes of Health.

BACKGROUND OF THE INVENTION

Genetic instability is now widely recognized as an essential factor in the evolution of cancer (Loeb, 1991; Lengauer et al., 1998). In the vast majority of solid tumors, this instability appears to involve gains and losses of whole chromosomes or large parts thereof, leading to aneuploidy (Lengauer et al., 1997; Duesberg et al., 1999). Recent evidence suggests that this form of chromosomal instability (CIN) is in some cases associated with alterations in a cell cycle checkpoint that monitors the integrity of the spindle apparatus, a structure critical for proper bipolar segregation of duplicated sister chromatids at mitosis (Cahill et al., 1999). A small fraction of CIN cancers are associated with dominant mutations in the human homolog of the yeast spindle checkpoint gene BUB1 (Cahill et al., 1998; Imai et al., 1999; Gemma et al., 2000). Likewise, mutations in the mouse BUB1 gene have been shown to disrupt the mitotic spindle checkpoint (Taylor and McKeon, 1997; Lee et al., 1999). Efforts to study the mitotic spindle checkpoint pathway through genetic approaches have been hampered by the extremely early embryonic lethality of mice homozygously deleted for MAD2 and BUB3, preventing the evaluation of chromosome loss rates in proliferating somatic cells (Dobles et al., 2000; Kalitsis et al., 2000). Recent evidence suggests that disruption of a single MAD2 allele can result in a modest increase in chromosomal instability associated with premature anaphase entry (Michel et al., 2001).

Intensive efforts to dissect the mitotic spindle checkpoint biochemically have elucidated a general mechanism by which BUB1 and other checkpoint proteins arrest mitotic progression in response to spindle damage (reviewed in Amon, 1999; Gardner and Burke, 2000). Specific MAD and BUB proteins are localized to the kinetochores of chromosomes that are unattached to the spindle apparatus (Chen et al., 1996; Li and Benezra, 1996; Taylor et al., 1998; Martinez-Exposito et al., 1999), suggesting that they trigger the checkpoint in cells exposed to microtubule inhibitors or in cells with spontaneously lagging chromosomes. At the biochemical level, the BUB and MAD protein kinase cascade ultimately impinges on a large multiprotein assembly known as the anaphase-promoting complex (APC) that appears to be the master regulator of chromosome segregation and mitotic exit in all eukaryotic cells (for reviews see King et al., 1996; Morgan, 1999; Peters, 1999). Although the mechanisms regulating APC activity are not yet completely understood, it seems clear that at least one outcome of activation of the MAD/BUB pathway is the association of MAD2 with the APC and its accessory factor Cdc20 (Fang et al., 1998). This association inhibits the intrinsic ubiquitinating activity of the APC$^{Cdc20}$ complex, thereby preventing the degradation of securin and later of cyclin B. Activation of the checkpoint thereby delays anaphase and exit from mitosis until all sister chromatids have established bipolar attachments to the spindle apparatus.

The securin proteins are key substrates of the APC pathway and comprise an evolutionarily divergent class of anaphase inhibitors. Members of the securin family include the Pds1 and Cut2 proteins in budding and fission yeast, respectively, the vertebrate pituitary-tumor transforming gene (PTTG or vSecurin) proteins, and the Pimples protein in *Drosophila* (Cohen-Fix et al., 1996; Funabiki et al., 1996b; Stratmann and Lehner, 1996; Zou et al., 1999). The securins form tight complexes with a well-conserved family of proteins, the 'sister-separating' proteases that have been termed separins (reviewed by Nasmyth et al., 2000; Yanagida, 2000). Securin degradation appears to be essential for sister chromatid separation, as expression of non-degradable securins blocks chromosome segregation in both budding and fission yeasts and in animal cells (Cohen-Fix et al., 1996; Funabiki et al., 1996b; Zou et al., 1999; Leismann et al., 2000). Current models propose that securin destruction liberates the active separin protease, allowing it to cleave proteins mediating sister chromatid cohesion, including the cohesin subunit Scc1 (Glotzer, 1999; Uhlmann et al., 1999; Nasmyth et al., 2000; Uhlmann et al., 2000; Waizenegger et al., 2000). This would release tension between paired kinetochores, allowing the separated sister chromatids to migrate poleward along the mitotic spindle.

Paradoxically, there is also evidence that securin plays a positive role in promoting sister separation. In fission yeast, loss of securin is lethal and produces the same effect as loss of separin itself, i.e., a complete block to chromosome segregation and completion of mitosis (Funabiki et al., 1996a). Similarly, *Drosophila* pimples mutants fail to separate sister chromatids during mitosis 15 (Stratmann and Lehner, 1996). Close examination of pds1 mutants in *S. cerevisiae* also demonstrates retarded anaphase entry and synthetic lethality with separin mutations (Ciosk et al., 1998), arguing that even in budding yeast, securin and separin may act synergistically rather than purely antagonistically in regulating anaphase.

There is a need in the art for therapeutic agents which are selectively toxic to aneuploid cells relative to euploid cells.

SUMMARY OF THE INVENTION

It is an object of the present invention to provide methods for screening for anti-cancer drugs.

It is another object of the invention to provide cell lines uselul for screening for anti-cancer drugs.

These and other objects of the invention are provided by one or more of the embodiments described below. In one embodiment of the invention, an isolated and purified homozygous securin-defective human cell line is provided.

In another embodiment of the invention a pair of isogenic cell lines is provided. A first cell line is homozygous securin-defective and a second cell line is securin-proficient.

In yet another embodiment of the invention a method of screening compounds to identify potential anti-cancer agents is provided. A test compound is contacted with each of the two isogenic cell lines. A first cell line is homozygous securin-defective and a second cell line is securin-proficient A test compound which preferentially kills the first cell line relative to the second cell line is identified as a potential anti-cancer agent.

These and other embodiments of the invention provide the art with new methods and cell lines for screening potential anti-tumor agents.

BRIEF DESCRIPTION OF THE DRAWINGS

The patent or application file contains at least one drawing executed in color. Copies of this patent or patent application publication with color drawings will be provided by the Office upon request and payment of the necessary fee.

FIGS. 1A to 1F. Generation of hSecurin$^{-/-}$ human cells by homologous recombination.

FIG. 1A. Schematic of knockout vector design with numbered black boxes denoting hSecurin exons.

FIG. 1B. PCR analysis of genomic DNA using STS A and STS B as primers and NEO ORF as a control.

FIG. 1C. Southern blot analysis confirms homozygous inactivation of the hSecurin locus.

FIG. 1D. Western blotting of hSecurin$^{-/-}$ and hSecurin$^{+/+}$ cell lysates with hSecurin-specific antibodies (arrows). (*) denotes a non-specific background band.

FIG. 1E. Flow cytometry analysis of hSecurin$^{+/+}$ and hSecurin$^{-/-}$ cells

FIG. 1F. Cell cycle distribution, apoptotic fraction, and mitotic index of exponentially growing hSecurin$^{+/+}$ and hSecurin$^{-/-}$ cells.

(FIG. 2F) Chromosome gains and losses in hSecurin$^{+/+}$ and hSecurin$^{-/-}$ cells. The number of FISH signals per cell was determined for chromosomes 7, 12, 17, and X. The fraction of cells with FISH signals equal to the modal value of two (chromosomes 7, 12, and 17) or the modal value of one (X chromosome) is cross-hatched. Non-modal cell populations accounting for 5 percent or more of the total are diagonal-hatched (for chromosome gains) and vertical-hatched (for chromosome losses). The total fraction of cells off the mode is given in the far-right column. Summary of the percentage of hSecurin$^{+/+}$ (HCT116) and hSecurin$^{-/-}$ (KO1, KO2) cells off the mode (FIG. 2G, top panel) and frequency of nuclear 'bud' structures in hSecurin$^{+/+}$ and hSecurin$^{-/-}$ cells (FIG. 2G, bottom panel).

FIGS. 3A to 3D. Multiplex-FISH analysis of CIN phenotype in hSecurin$^{-/-}$ cells.

FIG. 3A. M-FISH karyotype from a hSecurin$^{-/-}$ cell metaphase.

FIGS. 3B–D. Summary of M-FISH data from parental hSecurin$^{+/+}$ HCT116 cells (B) and from hSecurin$^{-/-}$ cells (C–D). Loss of a single copy of a given chromosome is vertical-hatched, loss of both copies is stippled, and gain of a single copy is diagonal-hatched.

FIGS. 4A to 4C. Defective execution of an a phase in hSecurin$^{-/-}$ cells.

FIGS. 4A–B. Time lapse microscopy of hSecurin$^{+/+}$ cells (A) and hSecurin$^{-/-}$ cells (B) stably expressing a histone H2B-GFP fusion protein. Arrows indicate aligned metaphase chromosomes, i.e., time 0.

FIG. 4C. Quantitative analysis of mitotic intervals in hSecurin$^{+/+}$ and hSecurin$^{-/-}$ cells.

FIG. 5A. Lysates from HeLa cells arrested with nocodazole and released for 1.5 or 2.5 hours (left panel) and from log phase hSecurin$^{+/+}$ and hSecurin$^{-/-}$ cells (right panel) were probed with antibodies to separin. The positions of the full-length (p200) and cleaved (p60) forms of separin are indicated. (*) mark a non-specific background band.

FIG. 5B. Cell cycle analysis of separin dynamics. hSecurin$^{+/+}$ cells (left panel) and hSecurin$^{-/-}$ cells (right panel) were synchronized by sequential thymidine-aphidicolin blocks, released at the indicated time points, and FACS analysis was performed.

FIG. 5C. Immunoblotting of synchronized cell lysates with antibodies to separin, phosphorylated histone H3, cyclin B, and the CDK inhibitor p21$^{WAF1/CIP1}$. Full-length (p200) and cleaved p60 separin are indicated. (*) indicate a non-specific band.

FIG. 6A. Immunoprecipitation of nocodazole-arrested HeLa cell and hSecurin$^{+/+}$ and hSecurin$^{-/-}$ HCT116 cell extracts with antibodies to separin followed by immunoblotting before (−) and after (+) incubation in mitotic Xenopus extracts as a source of active APC (Waizenegger et al., 2000). (*) mark a slower-migrating separin fragment seen in all six lanes of the in vitro assay.

FIGS. 6B–6C. Separin immunoprecipitates were incubated with mitotic Xenopus extracts, washed, and added to purified cohesin complexes. Samples were taken at different time points and analyzed by immunoblotting with myc antibodies. Full-length SCC1-myc migrates at ~150 kDa; a SCC1-myc cleavage product of 110 kDa (FIG. 6B). A 55 kDa Scc1 cleavage product (arrows) absent from reactions using separin isolated from hSecurin-deficient cells (FIG. 6C).

FIG. 6D. hSecurin$^{+/+}$ and hSecurin$^{-/-}$ HCT116 cells were transfected with Scc1-myc, nocodazole-synchronized in mid-mitosis, released from the nocodazole block and collected at the indicated time points. Lysates were analyzed by immunoblotting with myc antibody (top panels) and cyclin B antibody (bottom panels). Arrowhead marks the anaphase-specific 55 kDa Scc1-myc cleavage product. (*) indicates antibody cross-reacting band.

DETAILED DESCRIPTION OF THE INVENTION

Figure 1A:
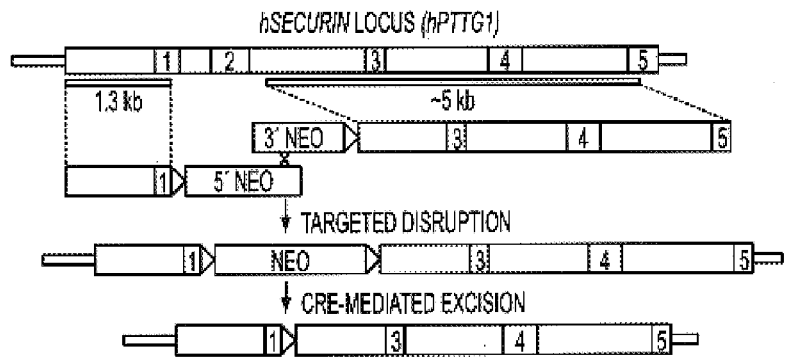

It is a discovery of the present inventors that homozygous securin-defective human cells are particularly useful for screening potential anti-tumor agents. Homozygous securin-defective cells fail to separate their metaphase chromosomes appropriately. As result, they have budded nuclei, chromosome instability, and gross aneuploidy. Chromosome instability and aneuploidy are characteristic features of many cancer cells.

A "securin gene-defective cell" lacks one or two wild-type securin gene alleles. Lack of two securin wild-type alleles may result, for example, in diminished expression of a securin gene or expression of a less functional securin protein. In a preferred embodiment, a securin gene-defective cell is homozygous, i.e., it lacks both wild-type securin gene alleles and is securin null.

Potential therapeutic agents can be screened for the ability to preferentially inhibit or kill homozygous securin-defective cells relative to securin-proficient cells. Potential therapeutic agents which can be tested include agents which are known in the art to have a pharmacological activity or can be compounds whose pharmacological activity is unknown. Compounds which can be tested include substances which are naturally occurring or which are designed in the laboratory, including members of small molecule libraries, protein libraries, nucleic acid libraries, etc. Test substances can be isolated from microorganisms, animals, or plants, or be produced recombinantly or by chemical synthesis. They can be purified or in mixtures in extracts. Therapeutic agents with known anti-tumor effects, such as cytosine arbinoside, fluorouracil, methotrexate or aminopterin, an anthracycline, mitomycin C, vinca alkaloids, demecolcine, etoposide, mithramycin, or an antitumor alkylating agent such as chlorambucil or malphalan can be tested for their efficacy against homozygous securin-defective cells. This test can be used to classify agents so that they can be specifically used for treating appropriate aneuploid or chromosome-unstable tumors.

An increase in the ratio of inhibition of growth of homozygous securin-defective cells compared to securin-proficient cells identifies the therapeutic or potential therapeutic agent as potentially useful for treating cancer. Preferably, the agents selected as potential therapeutic agents will kill or growth-inhibit securin-defective cells relative to securin-proficient cells in at least a 2:1, 5:1, 10:1, 20:1, or 50:1 ratio.

The ratio of inhibition or killing can be determined by any means known in the art. It is well known in the art that viable cells exclude dye. Viable cells can be observed to have an intact membrane and do not stain, where as dying or dead cells have "leaky" membranes and do stain. Any dyes known in the art can be used, such as, for example, trypan blue, eosin Y, naphthalene black, nigrosin, erythrosine B, and fast green. The ratio of killed or growth-inhibited homozygous securin-defective cells:securin-proficient cells can also be determinined by incorporation of labeled metabolites, such as, for example, $^3$H-thymidine. Cells can be cultured in medium containing radiolabeled metabolites; uptake or incorporation of the metabolites indicates cells growth.

Any means known in the art to generate a cell line which is homozygous securin defective can be used. (See, Waldman et al., 1996; Bunz et al., 1998; Chan et al., 1999; Rhee et al., 2000.) Any type of mammalian cell that can be maintained in culture or in an animal and can be transfected can be used to generate a securin gene-defective cell. These cells include, but are not limited to, primary cells, such as fibroblasts, myoblasts, leukocytes, hepatocytes, endothelial cells, and dendritic cells, as well as cell lines (e.g., NCI-BL2126, Hs 578Bst, HCC1954 BL, Hs 574.Sk, Hs888Lu, which are available from the American Type Culture Collection, 10801 University Boulevard, Manassas, Va. 20110-2209). Cells lines derived from brain, liver, lungs, kidney, spleen, lymph nodes, breast, colon, bladder, muscle, prostate, cervix, bone, or skin, can be used. Preferred cells include tumor cells, preferably human tumor, more preferably human colon tumor cells. Appropriate cells are, for example, colorectal cancer cells, present either in situ in a mammalian body or in vitro in a tissue culture preparation. Tumor cells can be isolated from patients and placed in tissue culture. Alternatively, established tumor cell lines, such as HT29, SW480, HCT116, DLD1, MCF-7, HL-60, HeLa cell S3, K562, MOLT-4, Burkitt's lymphoma Raji, A549, G361, M12, M24, M101, SK-MEL, U-87 MG, U-118 MG, CCF-STTG1, or SW1088 can be used. For example, a colorectal cancer cell line can be used to give rise to an isogenic securin cell line by homologous recombination. Any securin-proficient cell known in the art can be used to generate a homozygous securin-defective cell line. Preferably, the homozygous securin-defective cell is the same cell type (organ source) as the securin-proficient cell. More preferably, the two cell lines are isogenic.

Isogenic cell lines of the invention can be provided or maintained in a single, divided container, including, without limitation, a cell culture dish or flask, a liquid nitrogen container, a freezer box, a freezer, a refrigerator, a tissue culture hood, or an analytical device. They can be separated by any material or device. In some cases, the cell lines are separated spatially only.

As a downstream target of the mitotic spindle checkpoint, the sister chromatid separation pathway may be critically important for preventing aneuploidy in higher eukaryotes, particularly in those cells that have progressed along the multistep pathway leading to cancer (Kinzler and Vogelstein, 1996; Lengauer et al., 1998). Studies of hSecurin-deficient cells show that they exhibit high chromosome loss rates, similar to those observed in naturally occurring cancers. Thus, it would appear that hSecurin is indeed needed for chromosomal stability in humans. hSecurin deletion also retards chromosome separation. hSecurin is essential for the proper function and processing of the separin protease, for separin-dependent cleavage of the cohesin subunit Scc1, and for maintaining chromosomal stability in mammalian cells.

Mutations in the yeast PDS1 gene uncouple anaphase from the mitotic spindle checkpoint, allowing sister chromatid separation in cells treated with microtubule inhibitors (Yamamoto et al., 1996a; Ciosk et al., 1998). Similar experiments on hSecurin$^{-/-}$ cells found no evidence for chromatid separation in hsecurin$^{-/-}$ cells after prolonged incubation in nocodazole or colcemid. Thus it appears that the mitotic spindle checkpoint can inhibit sister chromatid separation in the absence of securin in mammalian cells, unlike the situation in budding yeast.

In contrast, deletion of hSecurin appears to inhibit the faithful execution of anaphase. This phenotype is similar to that observed in fission yeast and *Drosophila* with mutations in hSecurin homologs. Time lapse experiments and immunofluorescence microscopy show that hSecurin-deficient human cells appeared to carry out futile attempts at chromatid separation, resulting in an abnormal anaphase process (FIG. 4). This process results in cells with budded nuclei (FIG. 2G), chromosome instability (FIG. 2F), and gross aneuploidy (FIG. 3).

Figure 7:
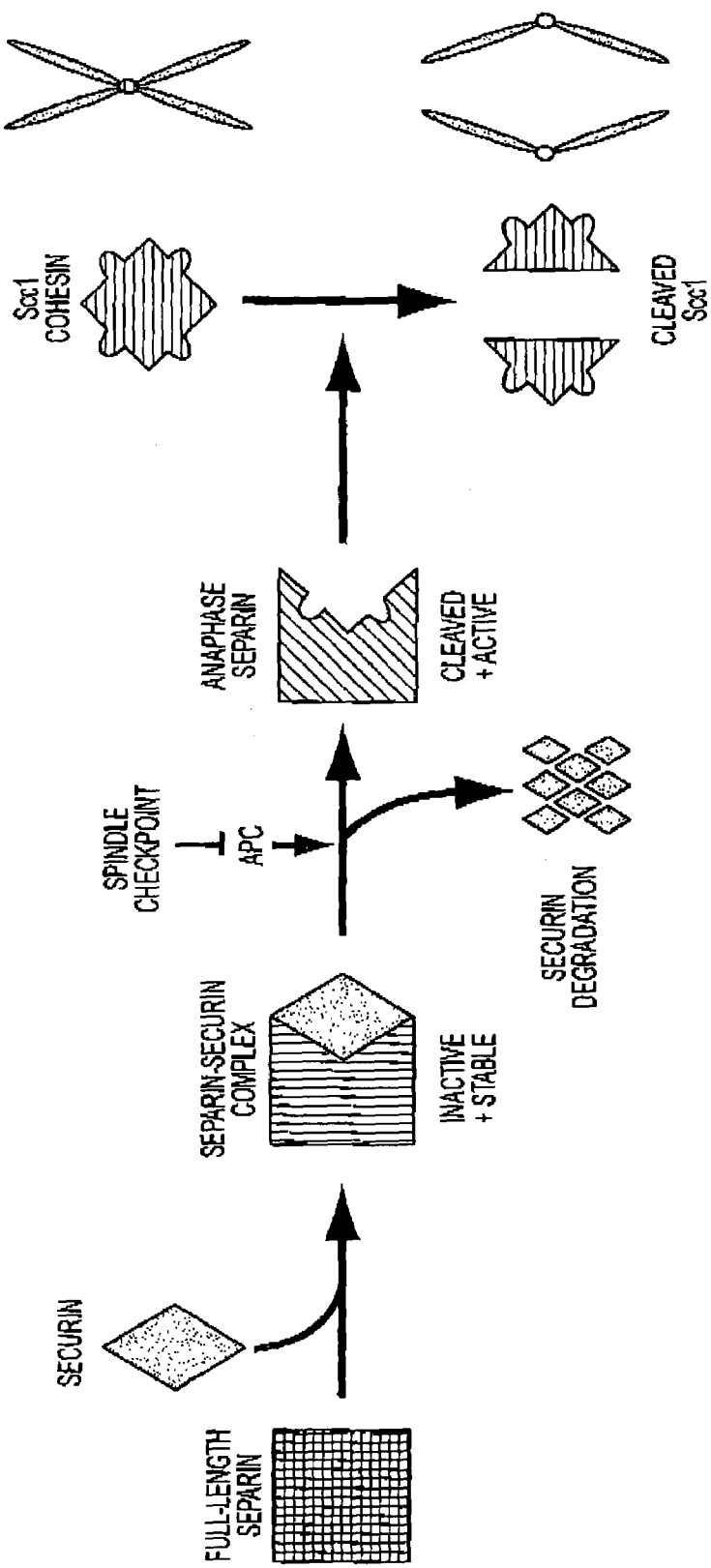
FIG. 7. Two-step 'Trigger Lock' model for the role of hSecurin in sister chromatid separation.

The biochemical analyses suggests a plausible two-step "trigger lock" model to explain these striking changes (FIG. 7). According to this model, full-length separin p200 binds to its inhibitor (securin) to "cock the trigger" for anaphase. APC activation then "pulls the trigger" by degrading securin and perhaps other proteins, allowing separin protease to be activated, cohesins to be cleaved, and chromatid segregation to occur. According to this model, separin that has never been bound to securin would be largely inactive - a safety lock on the trigger mechanism.

At least two possible mechanisms exist for the "cocking" of p200 separin by securin. Full-length separin p200 is likely stabilized by binding to securin, thereby explaining the reduced cellular levels of separin p200 observed in synchronized hSecurin$^{-/-}$ cells. However, this cannot be the sole mechanism of separin regulation, as logarithmically growing hSecurin$^{+/+}$ and hSecurin$^{-/-}$ cells, unperturbed by synchronization, have comparable levels of full-length p200 but dramatically different levels of the p60 cleavage product. This observation, together with in vitro cleavage data (FIG. 6A), indicates that hSecurin$^{-/-}$ cells have an additional defect in the APC-dependent proteolytic cleavage of full-length p200 separin to the p60 form.

Activation of APC at the metaphase-anaphase transition results both in activation of the separin protease and in its proteolytic cleavage to the mitosis-specific forms, suggesting that these two events are mechanistically coupled. Separin p60 may represent an activated form of the protease that fails to accumulate normally in the absence of hSecurin. There is much precedent for the concept that proteases are synthesized as large inactive polypeptides that become activated only after specific proteolytic cleavages under highly regulated conditions (e.g., zymogens and caspases; (Stennicke and Salvesen, 2000)). In support of this analogy is the recent finding that separins actually belong to the same family of cysteine proteases as the caspases (Uhlmann et al., 2000). Characterization of cleavage-site mutants of p200 separin will be crucial in resolving the role of proteolytic cleavage in the regulation of separin activity.

The morphologic observations described below were made on cells normally traversing mitosis in the absence of microtubule inhibitors or cell cycle blockers. It is important to note that anaphase eventually did occur in most of the hSecurin$^{-/-}$ cells under these circumstances. Although Scc1 cleavage was much less in hSecurin-deficient cells than in control cells, a low level of such cleavage was consistently observed. This suggests that a basal level of separin activity persists in these cells, which may explain why they remain viable.

Disruption of a single component of the complex of proteins responsible for sister chromatid cohesion (securin, separin, cohesins, Cdc20, APC components) can convert karyotypically stable euploid cells to unstable aneuploid ones. This instability involved the losses of whole chromosomes in the absence of the chromosome breaks and abnormal DNA repair processes that have also been invoked as potential causes of CIN. Genetic alterations resulting in inactivation of hSecurin have not been observed in human cancers, though this gene has been reported to be expressed at abnormally high levels in some cancers (Dominguez et al., 1998; Saez et al., 1999; Heaney et al., 2000). It is not difficult to genetically convert a chromosomally stable cancer cell into an unstable one that retains the capacity to proliferate robustly. A search for naturally occurring inactivating mutations in the genes that control chromatid cohesion and segregation may therefore provide further clues to the nature of CIN in human cancers.

A more complete understanding of the present invention can be obtained by reference to the following specific examples. These examples are provided for purposes of illustration only and are not intended to limit the scope of the invention.

EXAMPLE 1

Generation of Human Cells Lacking hSecurin

To evaluate hSecurin function, both copies of the hSecurin gene were inactivated via homologous recombination in HCT116 cells. HCT116 is a well-characterized human colorectal cancer cell line that has a stable karyotype and intact DNA damage and mitotic spindle checkpoints (Lengauer et al., 1997; Bunz et al., 1998). To obtain targeted deletions, vectors containing 5' and 3' elements derived from the hSecurin locus and an antibiotic resistance marker flanked by loxP sites (FIG. 1A) were transfected into HCT116 cells, and the resulting antibiotic-resistant clones were screened for proper integration as described in Experimental Procedures. Successfully targeted hSecurin$^{+/-}$ heterozygotes were transfected with a Cre recombinase plasmid to excise the antibiotic resistance marker and then re-transfected with the original targeting vectors to disrupt the remaining wild-type allele.

Figure 1B:
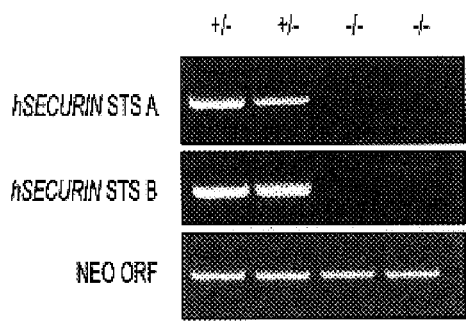

Genomic PCR analysis with two different sets of primers spanning the first intron and second exon of the hSecurin gene demonstrated homozygous deletions of these sequences in two different hSecurin$^{-/-}$ clones (FIG. 1B).

Figure 1C:
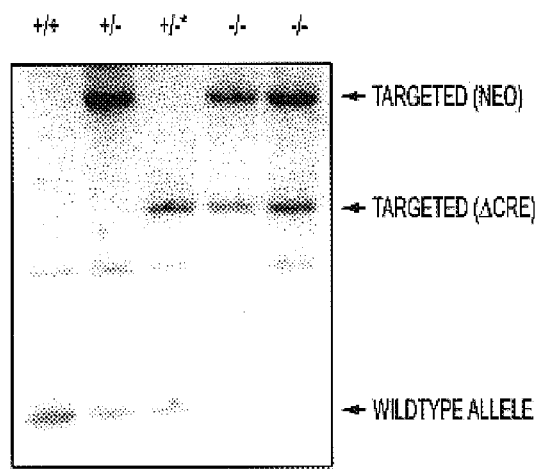

Southern blot analysis confirmed that both wild-type alleles had been inactivated through homologous recombination in these clones (FIG. 1C). Antibodies to hSecurin protein were made as described in Experimental Procedures. Immunoblotting with these antibodies demonstrated a lack of detectable protein in homozygously deleted cells while their isogenic controls expressed reactive polypeptides of the expected sizes (FIG. 1D). For the studies reported below, a total of three hSecurin$^{+/+}$ clones and two hSecurin$^{-/-}$ clones were tested. All cells of the same genotype behaved identically.

In culture, cells lacking hSecurin grew somewhat more slowly than wildtype cells, but the cell cycle distribution of unsynchronized cells, apoptotic fraction, and percentage of cells in mitosis were essentially identical for hSecurin$^{+/+}$ and hSecurin$^{-/-}$ clones (FIGS. 1E, 1F). Thus, remarkably, homozygous loss of hSecurin is not lethal to human cells.

EXAMPLE 2

Chromosomal Instability in hSecurin-Deficient Cells

Figure 2A:
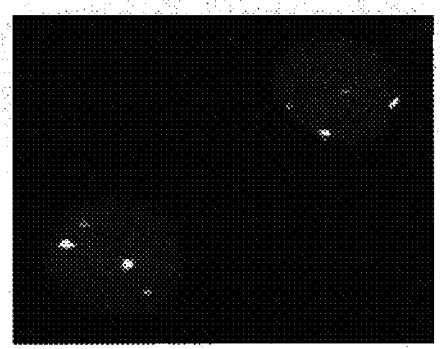
FIGS. 2A to 2G. Chromosomal instability in hSecurin$^{-/-}$ cells. FISH analysis of hSecurin$^{+/+}$ (FIG. 2A) and hSecurin$^{-/-}$ cells (FIGS. 2B–E) with probes specific for chromosome 7 (red) and chromosome 12 (green) (FIGS. 2A–D), or with a pan-centromeric probe (FIG. 2E). Nuclear DNA was stained with DAPI (blue).

To examine whether securin deficiency altered the rate of chromosome loss, hSecurin$^{-/-}$ cells (KO1 and KO2) and isogenic control cells (HCT116) were passaged for 20 generations and analyzed by fluorescent in situ hybridization (FISH) using chromosome-specific centromeric probes. As shown in FIG. 2, two fluorescent signals per autosomal chromosome per nucleus were observed in parental cells (FIG. 2A). The fraction of cells with signals more or less than the modal value of 2, which is a quantitative index of CIN (Lengauer et al., 1997), was typically 1–4% (FIG. 2F, 2G). In contrast, 17% to 32% of the hSecurin$^{-/-}$ cells exhibited aberrant numbers of signals per nucleus (FIG. 2F, 2G; examples in FIGS. 2B–D).

Figure 3A:
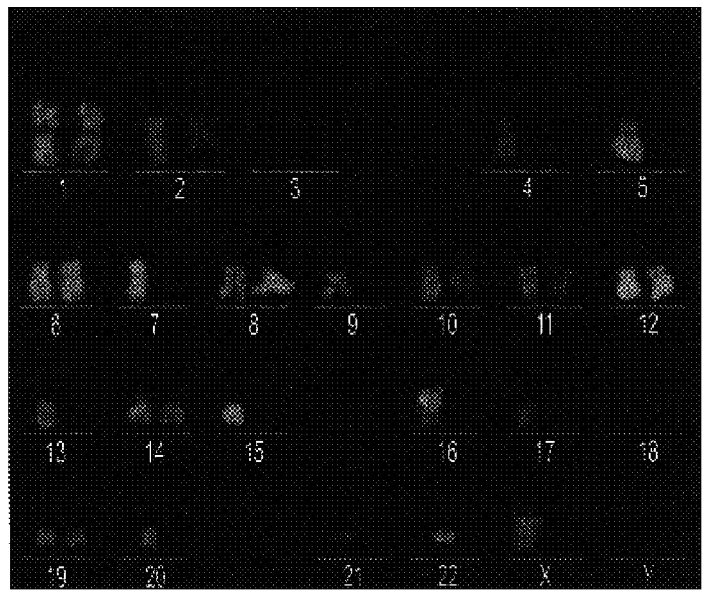
Figure 3B:
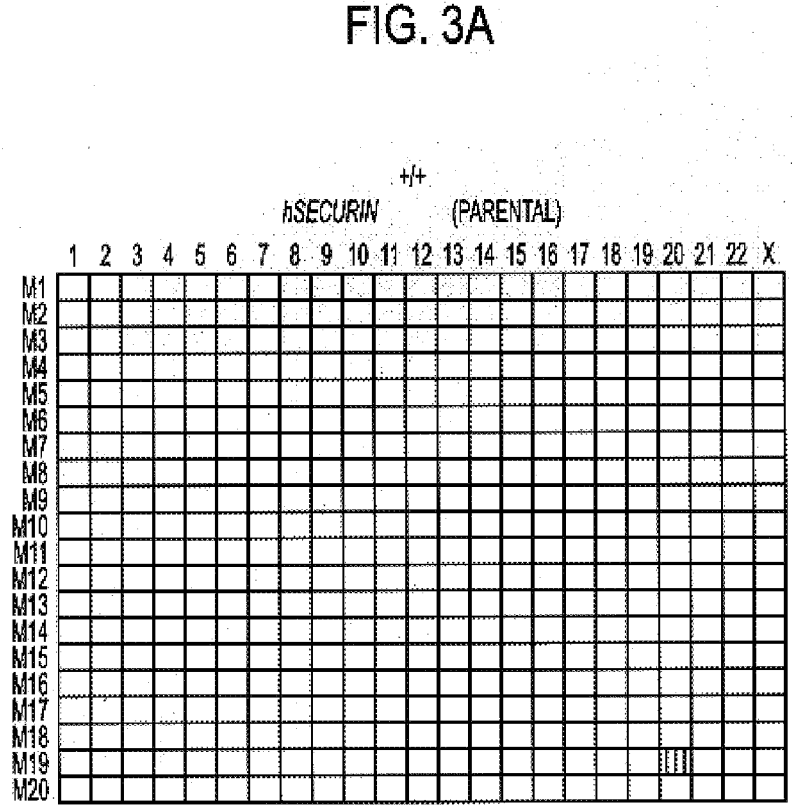
Figures 3C, 3D:
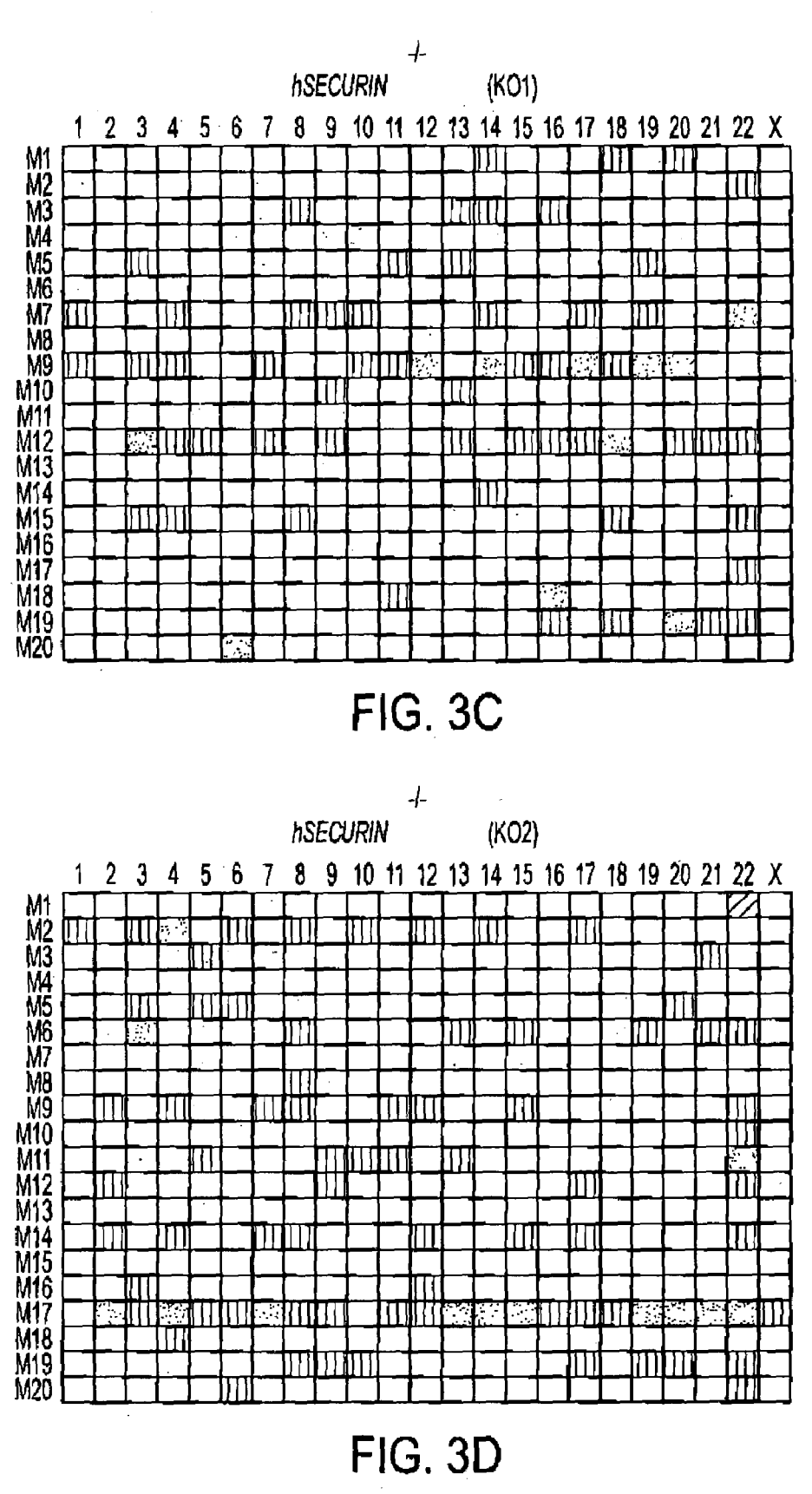

To confirm and extend these analyses, we employed multiplex-FISH (M-FISH) to paint entire metaphase spreads and inspect chromosomes for abnormalities of structure as well as number. M-FISH analysis was restricted to near-diploid metaphases to eliminate possible errors caused by misinterpretation of any pseudotetraploid cells arising sporadically in hSecurin$^{+/+}$ and hSecurin$^{-/-}$ cells. M-FISH karyotyping confirmed the clonal chromosome rearrangements reported previously in parental HCT116 cells (Masramon et al., 2000) and confirmed the stability of its near-diploid karyotype. Only a single metaphase with any chromosome loss was observed in 20 metaphase spreads (FIG. 3B). In contrast, hSecurin$^{-/-}$ cells contained many chromosome losses, with over 80% of metaphases exhibiting at least one chromosome loss and with individual metaphases missing as many as 21 chromosomes (FIGS. 3C, 3D; example in FIG. 3A). There was no chromosome immune from loss (FIGS. 3C, 3D), and the losses occurred without an increase in structural chromosomal abnormalities, as assessed by careful analysis of the M-FISH karyotypes.

Figure 2B:
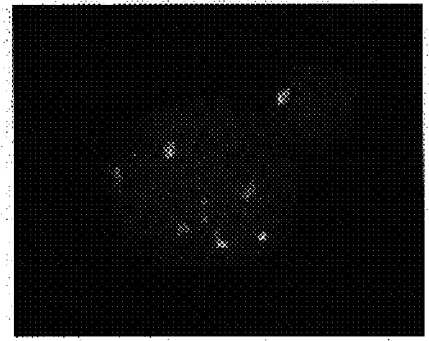
Figure 2C:
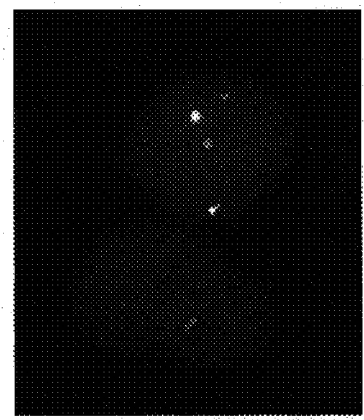
Figure 2D:
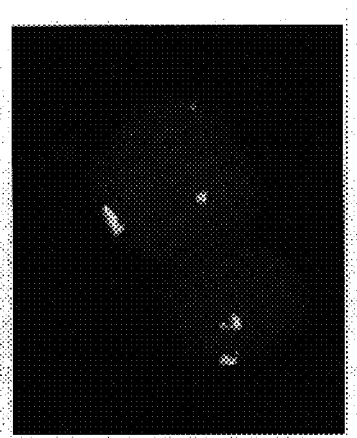
Figure 2E:
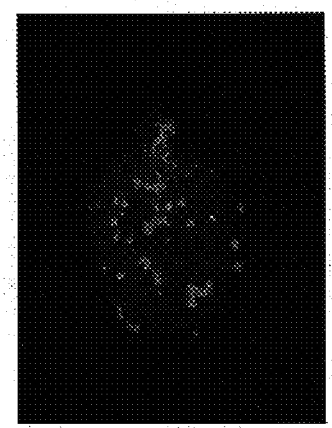
Figure 2F:
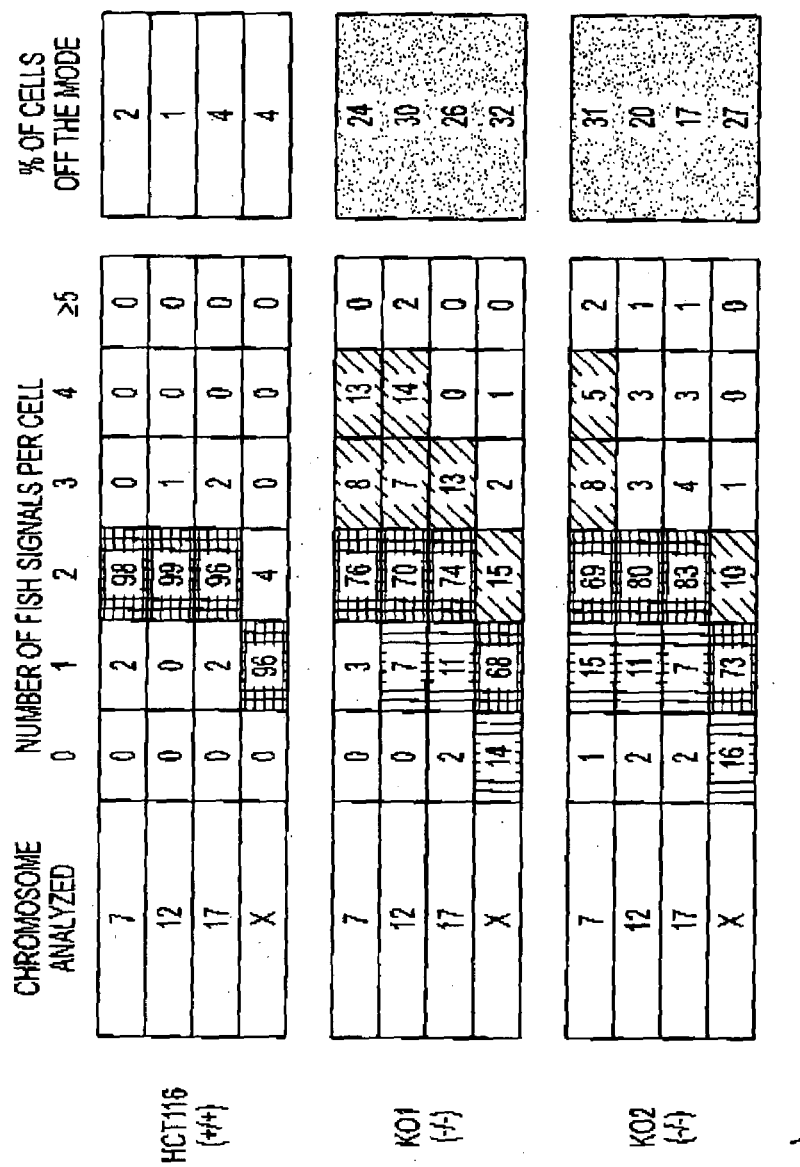
Figure 2G:
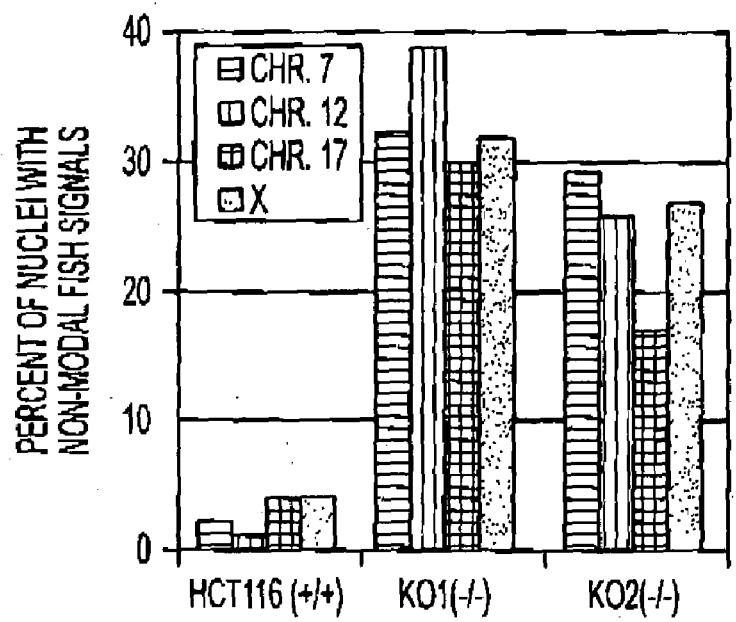
Figure 2G:
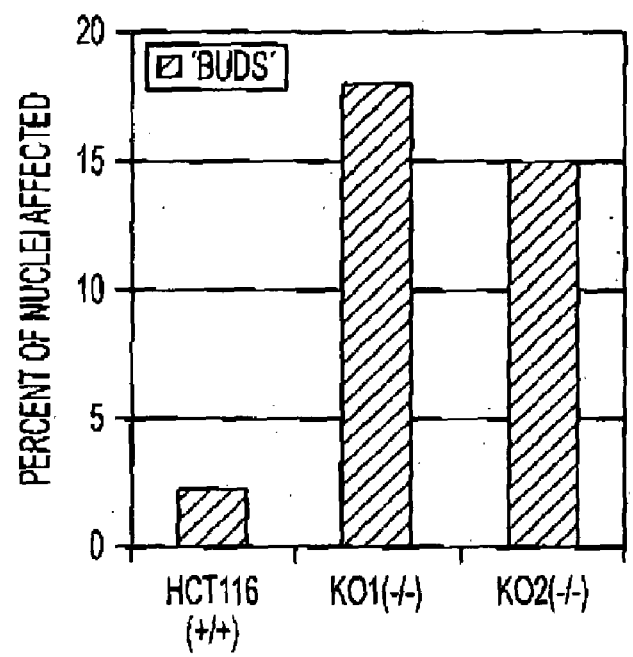

FISH analysis of interphase nuclei also demonstrated a peculiar cytological abnormality in hSecurin$^{-/-}$ cells: a 'bud' or accessory lobe reminiscent of a micronucleus but physically attached to the main nuclear body (FIG. 2B). This structure was found only rarely in control cells (FIG. 2G, right panel). In some cases, the chromosome-specific centromeric probes used for FISH analysis localized to this nuclear bud (FIG. 2B), suggesting that it had arisen through a defect in the dynamics of whole chromosomes. To confirm this observation, we performed FISH analysis using a probe that stained the centromeres of all chromosomes. The nuclear buds were found to contain a variable number of centromeric signals that were consistently detected even in very small buds (FIG. 2E).

EXAMPLE 3 hSecurin$^{-/-}$ Cells are Defective in the Execution of Anaphase

We first attempted to determine whether hSecurin loss resulted in chromatid separation in the presence of spindle poisons, as observed in yeast cells with Pds1 deficiency (Yamamoto et al., 1996b). Parental and hSecurin$^{-/-}$ cells were treated with nocodazole or colcemid and examined at various times thereafter by Hoechst dye staining as well as by FISH using centromeric probes. No evidence of sister chromatid separation was observed, even after 24 hours of nocodazole or colcemid treatment (e.g., FIG. 3A).

To examine normal mitotic processes in more detail, we expressed the histone H2B-GFP fusion protein (Kanda et al., 1998) in parental and hSecurin$^{-/-}$ cells. We were thereby able to monitor nuclear dynamics in vivo. Passage through mitosis is characterized by a series of visually dramatic cytological events, including rounding up of cell bodies, condensation of chromatin, dissolution of the nuclear membrane, alignment of chromosomes on the metaphase plate, and finally bipolar segregation of separated sister chromatids at anaphase. Time lapse microscopy in cells expressing histone H2B-GFP allowed us to examine these events under normal growth conditions.

The early events in mitosis, including chromatin condensation and midline congression of metaphase chromosomes, were similar in hSecurin$^{-/-}$ and control HCT116 cells. In control cells, the aligned chromosomes rapidly progressed into anaphase, characterized by sharp separation and bipolar segregation of sister chromatids (FIG. 4A). In contrast, over a third of hSecurin$^{-/-}$ cells failed to separate their metaphase chromosomes appropriately. In many cases, the GFP-stained nuclear material appeared to become stretched or deformed into two interconnected masses, giving rise to a 'dumbbell'-type morphology. The sharp separation between chromosomal masses that would indicate successful segregation of sister chromatids never appeared (FIG. 4B).

Despite their failure to execute anaphase, hSecurin$^{-/-}$ cells eventually exited mitosis, as the stretched chromatin masses decondensed to form the characteristic nuclear 'buds' seen in fixed cells (FIG. 4B, +60 min time point; compare with FIG. 2B). Phase-contrast microscopy demonstrated that these an a phase defective cells had exited mitosis without completing cytokinesis (data not shown).

Quantitative analysis of time lapse images was carried out to determine the relative timing of the anaphase delay in hSecurin$^{-/-}$ cells. The prophase-to-metaphase period (first sign of nuclear condensation to midline congression) and anaphase-to-telophase period (separation of chromosomes to nuclear decondensation) were fairly similar in both hSecurin$^{+/+}$ and hSecurin$^{-/-}$ cells (FIG. 4C). By contrast, the metaphase-to-anaphase period (midline congression to partial or total chromosome separation) was significantly increased in hSecurin$^{-/-}$ cells relative to the control cells (57 min versus 21 min; FIG. 4C).

To extend these results, we performed immunofluorescence experiments to examine the intranuclear distribution of centromeres during mitosis. hSecurin$^{+/+}$ and hSecurin$^{-/-}$ cells in various stages of mitosis were stained with anti-centromere antibodies (ACA). The parental HCT116 cells showed the expected patterns of centromere staining that are typical for the individual stages of mitosis. In prophase, hSecurin$^{-/-}$ cells also showed the characteristic 'double-dot' pattern indicative of paired centromeres. These paired centromeric signals then became tightly aligned, as would normally be expected during metaphase. In anaphase, however, the centromeres of hSecurin$^{-/-}$ cells were aberrantly distributed, in striking contrast to control cells. Several paired centromeric dots remained at the metaphase plate, despite the fact that most of the sister chromatids had already separated, as seen by the migration of the bulk of centromeric signals away from the metaphase plate and towards the two spindle poles. These results indicate that hsecurin$^{-/-}$ cells enter mitosis relatively normally, but then exhibit a major defect in the execution of anaphase.

EXAMPLE 4

Regulation of Sister-Separating and Chromatid Cohesion Proteins by hSecurin

Figure 5A:
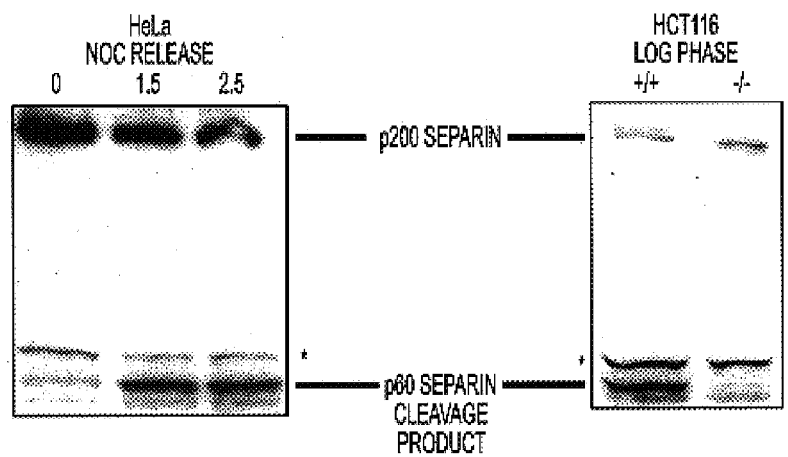
FIGS. 5A to 5C. Separin regulation is defective in hSecurin$^{-/-}$ cells.

We next explored the consequences of securin deficiency on the separin protease. As recently reported, human separin exists as several cell cycle regulated forms. During mitosis, separin undergoes proteolytic cleavage to produce carboxyl-terminal fragments containing the core 'separase domain' that is conserved among all separin proteins (Waizenegger et al., 2000; FIG. 5A, left panel). Intriguingly, the mitotic-specific p60 separin cleavage product was dramatically reduced in log phase hSecurin$^{-/-}$ cells (FIG. 5A, right panel).

Figure 5B:
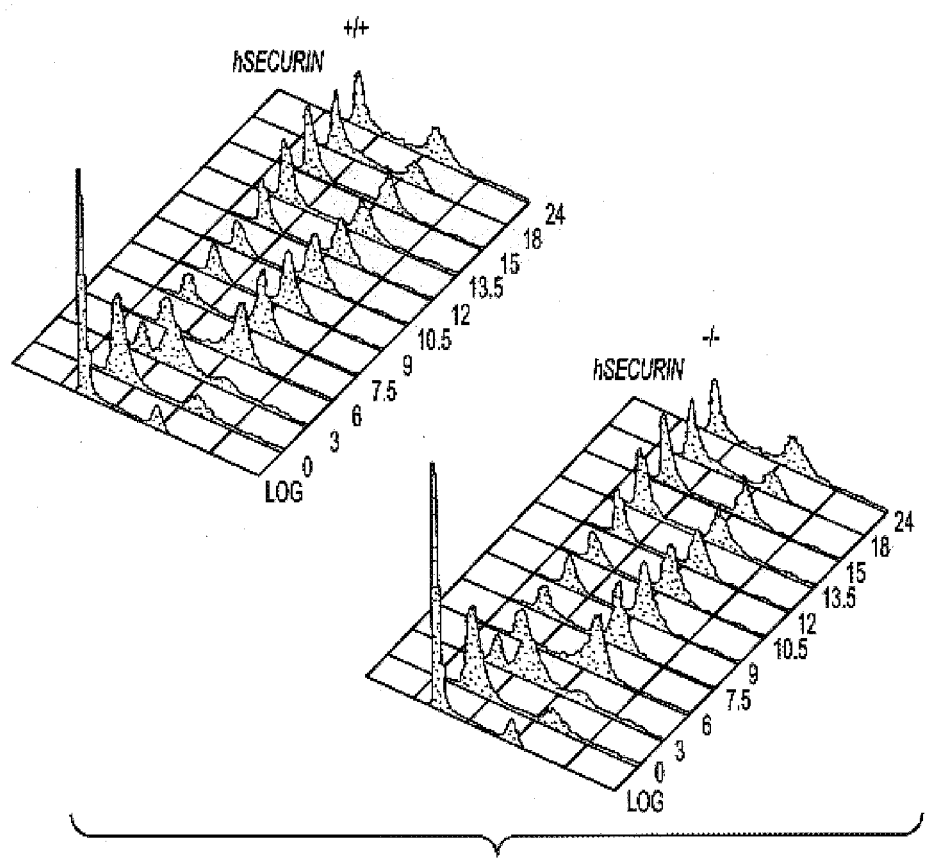
Figure 5C:
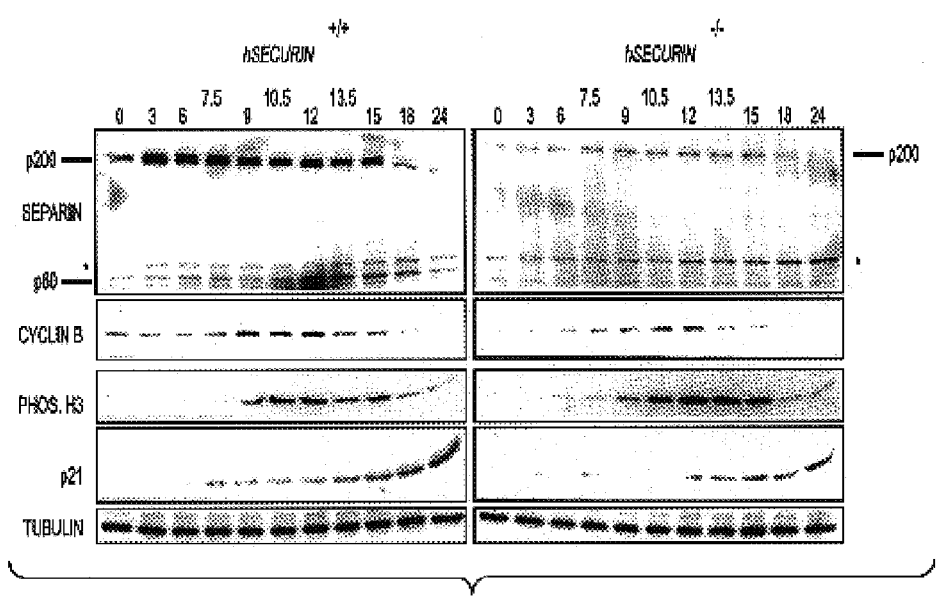

To confirm these results, separin cleavage was analyzed in cells synchronized by sequential thymidine-aphidicolin treatments. The synchronization and cell cycle progression were equivalent in hSecurin$^{+/+}$ and hSecurin$^{-/-}$ cells, as judged by FACS analysis (FIG. 5B) and by fluctuation in cyclin B and phosphorylated histone H3 (FIG. 5C). In control cells, the mitotic-specific separin p60 accumulated as cells progressed through mitosis, while the abundance of full-length separin declined (FIG. 5C, left panel; 12–24 hour time points). In synchronized hSecurin$^{-/-}$ cells, full-length separin p200 was also present, albeit at lower levels (FIG. 5C, right panel). As in control cells, the abundance of separin p200 declined as cells completed mitosis. However, the mitotic-specific p60 form of separin did not appear in hSecurin$^{-/-}$ cells, in stark contrast to the parental cells (FIG. 5C, right panel). The absence of detectable p60 cleavage product and the reduction in full-length separin p200 suggest that the cleavage and/or stability of separin is reduced in hSecurin$^{-/-}$ cells.

We next examined the cleavage of the human cohesin subunit Scc1, a substrate for separin. While the vast majority of Scc1 dissociates from chromosomes prior to metaphase in vertebrate cells, a small fraction remains bound to centromeric regions and appears to undergo site-specific cleavage at the onset of anaphase (Losada et al., 1998; Sumara et al., 2000). This cleavage reaction has been reconstituted in vitro using purified cohesins and immunoprecipitated separin complexes (Waizenegger et al., 2000).

Figure 6A:
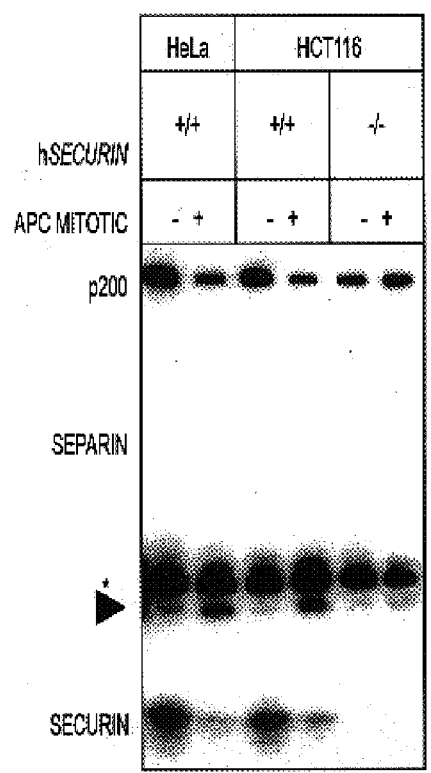
FIGS. 6A to 6D. Securin is necessary for APC-dependent proteolytic processing and activation of separin protease in vitro.

Extracts were prepared from nocodazole-arrested mitotic HCT116 hSecurin$^{+/+}$ and hSecurin$^{-/-}$ cells, and from mitotic HeLa cells as a control, and subjected to immunoprecipitation with antibodies to separin. In the presence of active *Xenopus* extracts as a source of mitotic APC, a fraction of full-length separin p200 was cleaved in samples from HeLa and hSecurin$^{+/+}$ HCT116 cells, as shown by the increased intensity of the p60 cleavage product and a decrease in the full-length p200 form (FIG. 6A). This reaction also triggered degradation of hSecurin in these samples (FIG. 6A). When the same experiment was performed side-by-side with immunoprecipitates from mitotic hSecurin$^{-/-}$ cells, the level of full-length separin p200 remained the same throughout the experiment and little if any increase in the separin cleavage products could be detected (FIG. 6A). This result suggests that APC-dependent cleavage of separin requires hSecurin, at least in vitro.

Figure 6D:
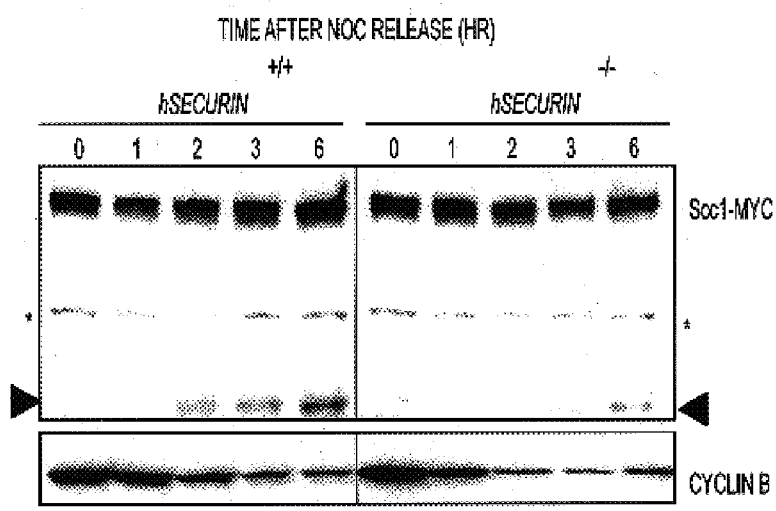
Figure 6B:
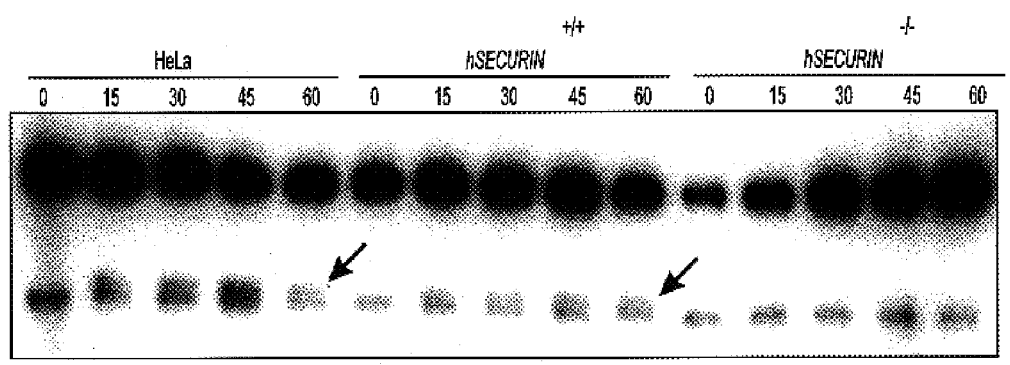
Figure 6C:
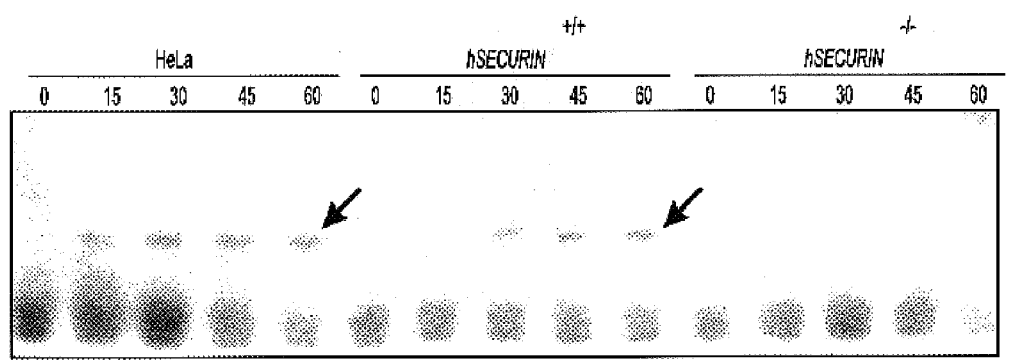

Next, the separin immunoprecipitates were incubated with purified cohesin in order to compare separin protease activity. Separin complexes isolated from both mitotic HeLa and HCT116 hSecurin$^{+/+}$ cells supported cleavage of the Scc1 cohesin subunit into at least two distinct products of about 110 and 55 kDa (FIGS. 6B, 6C). In contrast, separin complexes isolated from mitotic hSecurin$^{-/-}$ cells did not result in detectable amounts of either Scc1 cleavage fragment, even after a 60 minute incubation period (FIG. 6B, 6C).

To begin to address the physiological relevance of these in vitro observations, we examined whether hSecurin deficiency affected Scc1 cleavage in vivo. hSecurin$^{+/+}$ and hSecurin$^{-/-}$ cells were transfected with a myc epitope-tagged Scc1 expression vector (Waizenegger et al., 2000) and synchronized in a metaphase-like state with nocodazole. Following release from the nocodazole block, samples were collected at various time points, and the cleavage of Scc1-myc protein was assayed by immunoblotting. In hSecurin$^{+/+}$ cells, a 55 kDa cleavage product appeared about 2 hours after release (FIG. 6D, left panel). This time point corresponds to the onset of cyclin B degradation, a biochemical indicator of anaphase (FIG. 6D, left panel). By contrast, a much lower level of the 55 kDa cleavage product was observed in hSecurin$^{-/-}$ cells, even though cells continued to degrade cyclin B and exit mitosis (FIG. 6D, right panel; and data not shown).

EXAMPLE 5

Experimental Procedures

Inactivation of the hSecurin Locus by Homologous Recombination

Methods for generation of somatic cell knockouts in HCT116 have been described (Waldman et al., 1996; Bunz et al., 1998; Chan et al., 1999; Rhee et al., 2000) and were modified to generate hSecurin$^{-/-}$ cell lines. In brief, primers PTTG1-F1 and PTTG1-R3 were used to screen a human BAC library (Research Genetics) for genomic clones spanning the hSecurin/hPTTG1 locus. Elongase (Life Technologies) was used to amplify a 1.3 kb 5' targeting element (using primers PTTG1-Lforward and PTTG1-L1.3reverse) and a ~5 kb 3' targeting element (using primers PTTG1-Rforward and PTTG1-Rreverse). The resulting PCR products were cloned into the targeting vectors pFredA and pFredB, respectively, to create plasmids pFredA-PTTG1-L1.3 and pFredB-PTTG-R5. This new 'two-vector' targeting system was developed in an effort to reduce the background rate of Geneticin-resistant colonies arising from non-homologous integration events (F. Bunz, B. Vogelstein, K. Kinzler, manuscript in preparation). These constructs were digested with KpnI and SalI, respectively, and cotransfected into HCT116 cells using the Lipofectamine reagent (Life Technologies). Stably transfected cells were selected in McCoy's 5A medium supplemented with 10% fetal bovine serum (FBS) and 0.4 mg/ml Geneticin. Genomic DNA was isolated from pools of Geneticin-resistant clones (~10 clones/pool) and screened by PCR using primers PTTG1-A1 and NEO-reverse. Individual clones were obtained by limiting dilution of positive pools and rescreened by PCR. Candidate hSecurin$^{+/-}$ clones were confirmed by additional PCR analyses and by loss of a G/A polymorphism at nucleotide 1662 of the published genomic sequence (data not shown). Excision of the integrated loxP-NEO-loxP cassette was effected by transfection with a Cre recombinase expression plasmid (pΔE1-creHA) and isolation of individual Geneticin-sensitive clones. The remaining wild-type allele was inactivated by repeating the targeting procedure described above. Finally, four additional PCR primers (PTTG-F6, PTTG-R1; PTTG-gen01, PTTG-R4) were used to define two STS markers spanning the first intron and second exon of the hSecurin locus that were homozygously deleted in hSecurin$^{-/-}$ cells. For Southern blotting, genomic DNAs were digested with MseI, transferred to Zeta Probe membrane (Bio-Rad), and hybridized with a [$^{32}$P]-labeled probe corresponding to the 5' hSecurin targeting element. Additional details, including sequences of all PCR primers used in this paper, are available from the authors upon request.

Fluorescent in situ Hybridization (FISH) Analysis of Chromosome Loss

Methods for FISH analysis with chromosome-specific centromeric probes and quantitative analysis of chromosome loss rates have been described (Lengauer et al., 1997). A pan-centromeric FISH probe (IDbright Pan-Centromeric) was obtained from ID Labs Inc. and used according to the manufacturer's directions. Multiplex-FISH analysis of metaphase chromosome spreads was performed exactly as described (Speicher et al., 1996). The full karyotype of HCT116 cells was confirmed as 45,X,-Y, der(10)dup(10)(q24q26)t(10;16)(q26;q24), der(16)t(8;16)(q13;p13), der(18)t(17;18)(q21;p11.3).

Time Lapse Imaging of Mitosis in Live Cells

HCT116 and hSecurin$^{-/-}$ cells stably transfected with pBOS-histone H2B-GFP (Kanda et al., 1998) were analyzed on a Nikon TE200 Inverted microscope equipped with a heated stage and 40× objective. Images were acquired with a Princeton CCD camera at intervals ranging from 1 to 10 minutes and analyzed using the MetaMorph software program (Universal Imaging). For quantitation of mitotic intervals, the prophase-to-metaphase period was defined as the time elapsed from the first sign of nuclear condensation to midline alignment of chromosomes. The metaphase-to-anaphase period was defined as the interval from alignment to partial or total separation of chromatin into two masses, and the anaphase-to-telophase period was defined as the time from chromosome separation to nuclear decondensation.

Immunofluorescence Microscopy of Centromeres During Mitosis

Mitotic cells were obtained by gently tapping flasks of logarithmically growing hSecurin$^{+/+}$ and hSecurin$^{-/-}$ cells. Cells were washed with PBS and fixed for 10 minutes in 4% paraformaldehyde (in PBS). Aliquots of the cell suspension were cytocentrifuged onto glass slides and permeabilized in PBS +0.1% Triton X-100 for 5 minutes. Slides were incubated in blocking solution (10% fetal bovine serum in PBS) for 30 minutes. Human anti-centromere antibodies (ACA)

were obtained from Sigma (ANA-C) and used at a dilution of 1:25 in blocking solution for 60 minutes. Slides were then washed 3 times in PBS+0.05% Tween-20 and incubated with Alexa 488-conjugated anti-human secondary antibody (Molecular Probes) at 1:100 for 60 minutes. Slides were washed as above, counterstained with DAPI, and mounted in antifade solution prior to fluorescence microscopy.

Cell Cycle Synchronization, FACS Analysis, and Immunoblotting

Cells were synchronized at the G1/S phase transition by sequential thymidine and aphidicolin blocks. Briefly, cells were cultured in McCoy's 5A medium plus 10% FBS supplemented with 2.5 mM thymidine for 18 hours, then washed twice with Hank's balanced salt solution (HBSS) and incubated in McCoy's medium plus 10% FBS. After 8 hours, aphidicolin was added to a final concentration of 2 µg/ml. After 15 hours, cells were washed twice with HBSS and incubated in fresh McCoy's medium +10% FBS. At various time points, cells were harvested and washed with ice-cold phosphate-buffered saline. A portion of harvested cells was fixed and stained in formaldehyde/Hoechst 33258 solution (Bunz et al., 1998), and the remaining cells were frozen at −80° C. FACS analysis was performed on a LSR Flow Cytometer (Becton Dickinson) using the CellQuest software package.

Protein extracts were prepared by lysing cells on ice in HB2 buffer (50 mM HEPES, pH 7.5, 0.5% NP-40, 10% glycerol, 100 mMNaCl, 10 mM Na pyrophosphate, 5 mM β-glycerophosphate, 50 mM NaF, 0.3 mM $Na_3VO_4$, 1 mM DTT, 1 mM PMSF, and 1× complete protease inhibitor cocktail (Roche)), followed by brief sonication and centrifugation at 10,000× g for 15 minutes at 4° C. Immunoblotting was performed on Immobilon P membranes (MilliPore) according to the manufacturer's instructions. Antibodies to hSecurin were generated by immunizing rabbits with peptides VDKENGEPGTRVVAKDGLC and LDEERELEK-LFQLGC, followed by affinity purification on a peptide matrix (QCB/BioSource). Antibodies to human Scc1 and separin have been described (Waizenegger et al., 2000). Commercially available antibodies to cyclin B (Santa Cruz), phosphorylated histone H3 (Upstate Biotechnology), p21$^{WAF1/CIP1}$ and α-tubulin (Oncogene Science) were used as recommended by the manufacturers. Signals were developed using the Renaissance Plus Enhanced Chemiluminescence Reagent (New England Nuclear).

Scc1 Cleavage Assays Using Purified Components

Purification of human cohesin complexes and in vitro cleavage assays were performed as described (Waizenegger et al., 2000). Briefly, separin complexes were immunoprecipitated from extracts derived from nocodazole-arrested HeLa or HCT116 hSecurin$^{+/+}$ and hSecurin$^{-/-}$ cells. Because separin abundance was lower in nocodazole-arrested hSecurin-deficient cells than in controls, a four-fold excess of hSecurin$^{-/-}$ cell extract was used in some experiments. The immobilized separin complexes were incubated in mitotic *Xenopus* egg extracts, washed, and then mixed with purified cohesin. Aliquots of the reaction mixture were withdrawn at various times and added to SDS-PAGE sample buffer for subsequent analysis of Scc1 cleavage by immunoblotting.

Scc1 Cleavage in vivo

An expression plasmid encoding human Scc1 tagged at the carboxy terminus with 9 copies of the myc epitope (pcDNA-hScc1-myc) was transfected into HCT116 hSecurin$^{+/+}$ and hSecurin$^{-/-}$ cells. Approximately 24 hours after transfection, 0.2 µg/ml nocodazole was added to arrest cells in a metaphase-like state. After 15 to 18 hours, cells were washed three times with HBSS and returned to nocodazole-free medium. Cells were harvested at the indicated time points. Preparation of cell lysates and detection of Scc1-myc cleavage products by immunoblotting were performed as described above.

REFERENCES

1. Amon, A., Curr Opin Genet Dev 9, 69–75 (1999).
2. Bunz, F., et al., Science 282, 1497–501 (1998).
3. Cahill, D. P., et al., Trends Cell Biol 9, M57–60 (1999).
4. Cahill, D. P., et al., Nature 392, 300–3 (1998).
5. Chan, T. A., et al., Nature 401, 616–20 (1999).
6. Chen, R. H., et al,. Science 274, 242–6 (1996).
7. Ciosk, R., et al., Cell 93, 1067–76 (1998).
8. Cohen-Fix, O., et al., Genes Dev 10, 3081–93 (1996).
9. Dobles, M., et al., Cell 101, 635–45 (2000).
10. Dominguez, A., et al., Oncogene 17, 2187–93 (1998).
11. Duesberg, P., et al., Anticancer Res 19, 4887–906 (1999).
12. Fang, G., et al., Genes Dev 12, 1871–83 (1998).
13. Funabiki, H., et al., Embo J 15, 6617–28 (1996).
14. Funabiki, H., et al., Nature 381, 438–41 (1996).
15. Gardner, R. D., and Burke, D. J. Trends Cell Biol 10, 154–8 (2000). 16. Gemma, A., et al., Genes Chromosomes Cancer 29, 213–8 (2000).
17. Glotzer, M., Curr Biol 9, R531–4 (1999).
18. Heaney, A. P., et al., Lancet 355, 716–9 (2000).
19. Imai, Y., et al., Jpn J Cancer Res 90, 837–40 (1999).
20. Kalitsis, P., et al., Genes Dev 14, 2277–82 (2000).
21. Kanda, T., et al., Curr Biol 8, 377–85 (1998).
22. King, R. W., et al., Science 274, 1652–9 (1996).
23. Kinzler, K. W., and Vogelstein, B., Cell 87, 159–170 (1996).
24. Lee, H., et al., Mol Cell 4, 1–10 (1999).
25. Leismann, O., et al., Genes Dev 14, 2192–205 (2000).
26. Lengauer, C., Kinzler, K. W., and Vogelstein, B., Nature 386, 623–7 (1997).
27. Lengauer, C., Kinzler, K. W., and Vogelstein, B., Nature 396, 643–9 (1998).
28. Li, Y., and Benezra, R., Science 274, 246–8 (1996).
29. Loeb, L. A., Cancer Res 51, 3075–9 (1991).
30. Losada, A., et al., Genes Dev. 14, 1986–97 (1998).
31. Martinez-Exposito, M. J., et al., PNAS USA 96, 8493–8 (1999).
32. Masramon, L., et al., Cancer Genet Cytogenet 121, 17–21 (2000).
33. Morgan, D. O., Nat Cell Biol 1, E47–53 (1999).
34. Michel, L. S., et al., Nature 409, 355–359 (2001).
35. Nasmyth, K., Peters, J. M., and Uhlmann, F., Science 288, 1379–85 (2000).
36. Peters, J. M., Exp Cell Res 248, 339–49 (1999).
37. Rhee, I., et al, Nature 404, 1003–7 (2000).
38. Saez, C., et al., Oncogene 18, 5473–6 (1999).
39. Speicher, M. R., et al., Nat Genet 12, 368–75 (1996).
40. Stennicke, H. R., and Salvesen, G. S., Biochim Biophys Acta 1477, 299–306 (2000).
41. Stratmann, R., and Lehner, C. F., Cell 84, 25–35 (1996).
42. Sumara, I., et al., J. Cell Biol. 151, 749–762 (2000).
43. Taylor, S. S., Ha, E., and McKeon, F., J Cell Biol 142, 1–11 (1998).
44. Taylor, S. S., and McKeon, F., Cell 89, 727–35 (1997).
45. Uhlmann, F., Lottspeich, F., and Nasmyth, K., Nature 400, 37–42 (1999).
46. Uhlmann, F., et al., Cell 103, 375–386 (2000).
47. Waizenegger, I. C., et al., Cell 103, 399–410 (2000).
48. Waldman, T., et al., Nature 381, 713–16 (1996).

49. Yamamoto, A., Guacci, V., and Koshland, D., J Cell Biol 133, 99–110 (1996).
50. Yamamoto, A., Guacci, V., and Koshland, D., J Cell Biol 133, 85–97 (1996).
51. Yanagida, M., Genes Cells 5, 1–8 (2000).
52. Zou, H., et al., Science 285, 418–22 (1999).

We claim:

1. A method of screening compounds to identify potential anti-cancer agents, comprising:
   contacting a test compound with each of two isogenic mammalian cell lines, wherein the first cell line is homozygous securin-defective and the second cell line is securin-proficient; and
   identifying as a potential anti-cancer agent a test compound which preferentially inhibits growth of the first cell line relative to the second cell line.

2. The method of claim 1 wherein the test compound is identified as a potential anti-cancer agent if it inhibits growth of the first cell line at least 2-fold more than the second cell line.

3. The method of claim 1 wherein the test compound is identified as a potential anti-cancer agent if it inhibits growth of the first cell line at least 5-fold more than the second cell line.

4. The method of claim 1 wherein the test compound is identified as a potential anti-cancer agent if it inhibits growth of the first cell line at least 10-fold more than the second cell line.

5. The method of claim 1 wherein the test compound is identified as a potential anti-cancer agent if it inhibits growth of the first cell line at least 20-fold more than the second cell line.

6. The method of claim 1 wherein the test compound is identified as a potential anti-cancer agent if it inhibits growth of the first cell line at least 50-fold more than the second cell line.

7. The method of claim 1 wherein the cell lines are in culture when contacted with the test compounds.

8. The method of claim 1 wherein the cell lines are in xenografts when contacted with the test compound.

9. The method of claim 1 wherein the test compound preferentially kills the first cell line relative to the second cell line.

10. The method of claim 1 wherein the two isogenic cells lines are human cell lines.

* * * * *